(12) United States Patent
Chai et al.

(10) Patent No.: US 12,292,594 B2
(45) Date of Patent: May 6, 2025

(54) MULTI-FIBER LIGHT GUIDE, DEVICE WITH A MULTI-FIBER LIGHT GUIDE AND METHOD FOR PRODUCING THE SAME

(71) Applicant: Schott AG, Mainz (DE)

(72) Inventors: Wee Kiat Chai, Singapur (SG); Robert Hettler, Kumhausen (DE); Julia Weisshuhn, Mainz (DE); Jan Philipp Steigleder, Budenheim (DE)

(73) Assignee: Schott AG, Mainz (DE)

( * ) Notice: Subject to any disclaimer, the term of this patent is extended or adjusted under 35 U.S.C. 154(b) by 250 days.

(21) Appl. No.: 17/975,979

(22) Filed: Oct. 28, 2022

(65) Prior Publication Data

US 2023/0067347 A1 Mar. 2, 2023

Related U.S. Application Data

(63) Continuation-in-part of application No. PCT/EP2021/060852, filed on Apr. 26, 2021.

(30) Foreign Application Priority Data

Apr. 30, 2020 (EP) ..................................... 20172235

(51) Int. Cl.
*G02B 6/02* (2006.01)
*A61B 5/024* (2006.01)
(Continued)

(52) U.S. Cl.
CPC ...... *G02B 6/02395* (2013.01); *A61B 5/02427* (2013.01); *A61B 5/02438* (2013.01);
(Continued)

(58) Field of Classification Search
CPC .. G02B 6/0011; G02B 6/02042; G02B 6/036; C03C 25/602
See application file for complete search history.

(56) References Cited

U.S. PATENT DOCUMENTS 3,582,297 A 6/1971 Lakeman
3,830,640 A 8/1974 Kitano et al.
(Continued)

FOREIGN PATENT DOCUMENTS

DE 198 30 335 A1 1/1999
GB 1 289 673 A 9/1972

OTHER PUBLICATIONS

International Search Report dated Jul. 20, 2021 for International Application No. PCT/EP2021/060852 (3 pages).

*Primary Examiner* — Rhonda S Peace
(74) *Attorney, Agent, or Firm* — TAYLOR & EDELSTEIN (57) ABSTRACT

A multi-fiber light guide includes: light guiding fibers, each fiber including an elongated glass core; a glass cladding, the cores being surrounded by the cladding to form a rigid and continuous glass element, the cores having a higher refractive index than the cladding such that light can be guided by a total reflection along the cores, which end in two abutting faces of the glass element such that light can be guided along the cores from one abutting face to the other abutting face; and an ion exchange layer at each of the abutting faces, the glass of the cores and the glass of the cladding including alkali ions, which are at least partly exchanged by alkali ions of a higher atomic number within the ion exchange layer at the abutting faces, the exchanged alkali ions within the ion exchange layer imparting a compressive stress at the abutting faces.

14 Claims, 5 Drawing Sheets

(51) Int. Cl.
*C03B 37/012* (2006.01)
*C03B 37/027* (2006.01)
*C03C 13/04* (2006.01)
*C03C 25/602* (2018.01)
*G01J 1/04* (2006.01)

(52) U.S. Cl.
CPC ...... *C03B 37/01214* (2013.01); *C03B 37/027* (2013.01); *C03C 13/04* (2013.01); *C03C 25/602* (2013.01); *G01J 1/0425* (2013.01); *C03B 2203/40* (2013.01)

(56) References Cited

U.S. PATENT DOCUMENTS

| | | | |
|---|---|---|---|
| 8,789,998 B2* | 7/2014 | Schneider | G02B 6/0031 362/330 |
| 8,974,105 B2* | 3/2015 | Schneider | G02B 6/0031 362/330 |
| 11,573,450 B1* | 2/2023 | Jones | G02F 1/133524 |
| 2006/0008220 A1 | 1/2006 | Reichel et al. | |
| 2008/0069505 A1 | 3/2008 | Reichel et al. | |
| 2015/0064472 A1 | 3/2015 | Gross et al. | |
| 2015/0153510 A1 | 6/2015 | Ohara et al. | |
| 2019/0076036 A1 | 3/2019 | Lasarov et al. | |
| 2019/0154915 A1 | 5/2019 | Sugawara | |
| 2023/0067347 A1* | 3/2023 | Chai | C03B 37/027 |

* cited by examiner

MULTI-FIBER LIGHT GUIDE, DEVICE WITH A MULTI-FIBER LIGHT GUIDE AND METHOD FOR PRODUCING THE SAME

CROSS REFERENCE TO RELATED APPLICATIONS

This is a continuation of PCT application no. PCT/EP2021/060852, entitled "MULTI-FIBER LIGHT GUIDE, DEVICE WITH A MULTI-FIBER LIGHT GUIDE AND METHOD FOR PRODUCING THE SAME", filed Apr. 26, 2021, which is incorporated herein by reference. PCT application no. PCT/EP2021/060852 claims priority to European patent application no. 20172235.2, filed Apr. 30, 2020, which is incorporated herein by reference.

BACKGROUND OF THE INVENTION

1. Field of the Invention

This present invention generally concerns fiber optical light guides. Specifically, the present invention relates to fiber optical devices with a multitude of fused light guiding fibers.

2. Description of the Related Art

One type of fiber optical light guides composed of fused optical fibers is a fiber optical face plate. US 2008/0069505 Al discloses a pixel display covered with a fiber optical faceplate which is mounted in a distance to the pixels. Further, US 2006/0008220 Al describes an optical low-pass filter using a fiber face plate.

Fiber optical plates used in front of displays may serve to increase or decrease the viewing angle or generally to shift the image plane relative to the display. In a faceplate, the individual fibers are fused together so that the longitudinal direction of the fibers lies transverse to the faces of the faceplate. As the fibers are fused together in direction perpendicular to the faces of the faceplate, the fusing areas may provide weakening zones extending transversely through the plate. Further, the glasses for fiber optical light guides are chosen because of their optical properties. Thus, suitable glasses may not necessarily be the strongest glasses in terms of mechanical stability. Thus, rigid multi-fiber light guides are prone to breakage upon mechanical stress, in particular by an impact or shock.

What is needed in the art is a multi-fiber light guide with an improved mechanical stability to avoid breakage.

SUMMARY OF THE INVENTION

The present invention provides a multi-fiber light guide, including a multitude of light guiding fibers, each of the fibers including an elongated glass core. The cores are surrounded by a glass cladding so that the cladding with the cores form a rigid continuous glass element. The cores have a higher refractive index than the cladding so that light can be guided by total reflection along the glass cores. The glass element (9) of the multi-fiber light guide has two abutting faces, with the cores ending in both abutting faces, so that light can be guided along the cores from one abutting face to the other. Further, the glasses of the cores and the cladding contain alkali ions. The alkali ions of the glasses are at least partly exchanged by alkali ions of a higher atomic number within an ion exchange layer at each of the abutting faces. This way, the exchanged alkali ions within the ion exchange layer impart a compressive stress at the abutting faces. Thus, a multi fiber light guide is provided which has chemically strengthened abutting faces. It has been surprisingly found that a continuous layer with compressive stress can be formed at the abutting faces although the glasses of the cores and the cladding differ in their chemical composition.

The ion exchange layer extends into the glass of the cores, the cladding and/or a shell, which circumferences the cores and the cladding. Advantageously, the ion exchange layer penetrates the glass cores, the glass cladding and/or the glass shell. Beneficially, the penetration depth of the ion-exchange layer in the glass cores is different, in particular smaller than the penetration depth of the ion-exchange layer in the glass cladding. The shell provides additional mechanical stability against stresses from outside of the multi-fiber light guide, especially against lateral induced stresses.

According to one embodiment, the glass element forming the multi-fiber light guide is a plate or disc, respectively. In this embodiment with a plate shaped or disc shaped glass element the abutting faces of the light guide are typically closer together than the longest lateral dimension of the glass element. Accordingly, the thickness of the disc or plate is smaller than the longest lateral dimension. As the thickness of the disc defines the length of fibers, similarly, the length of the light guiding fibers is smaller than the longest lateral dimension. A multi-fiber light guide of this type will be referred to as a faceplate. Optionally, this condition also holds for the shortest lateral dimension of the disc or plate. Thus, optionally, the thickness of the plate or the length of the fibers or cores is smaller than the shortest lateral dimension of the disc.

According to a further embodiment, the multi-fiber light guide has an elongated shape. In this embodiment, the fiber length is greater than the largest lateral dimension of the glass element.

The multi-fiber light guide, a method for producing the same and devices including the light guide are hereinafter described in detail and with reference to the figures.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplification set out herein illustrate embodiment of the invention, and such exemplifications are not to be construed as limiting the scope of the invention in any manner.

DETAILED DESCRIPTION OF THE INVENTION

Figure 1:
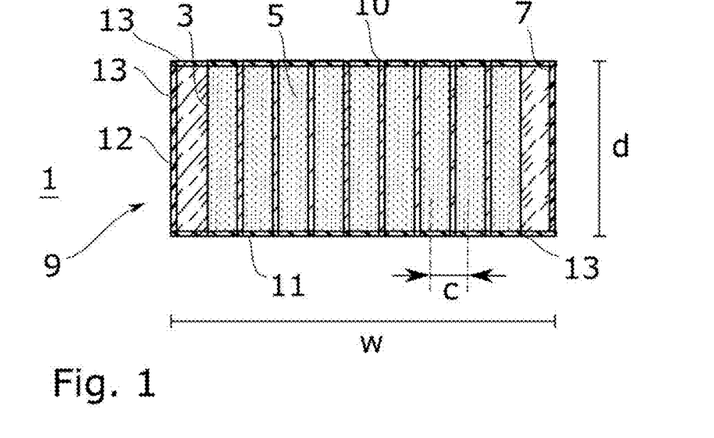
FIG. 1 shows a multi-fiber light guide in a cross-sectional view.

FIG. 1 shows an example of a multi-fiber light guide 1 having a disc or plate like shape. In this embodiment, the width w or its lateral dimension is generally larger than the thickness d or length of the light guide 1.

Generally, the light guide 1 includes a multitude of light guiding fibers 3. Without restriction to the specific embodiment, the fibers 3 are arranged side by side so that their longitudinal directions are generally parallel to each other. The fibers 3 include a core 5 embedded into a cladding 7. The glasses of core 5 and cladding 7 are fused together so that the cores 5 and the cladding 7 form a continuous rigid glass element 9. Optionally, the individual fibers are of microscopic size to enable transfer of optical signals with high spatial resolution. According to one embodiment which is not restricted to the specific example shown in FIG. 1, the pitch or center-to center distance c of adjacent light guiding fibers 3 is from 2 μm to 500 μm, optionally at most 200 μm. Optionally, the width of the cladding 7 between the cores 5 is larger than 0.5 μm, optionally larger than 1 μm, optionally larger than 1.5 μm. In some cases, the width of the cladding 7 between the cores 5 may be larger than 2 μm.

The light guiding fibers 3 end in both opposing abutting faces 10, 11 of the glass element 9. This way, as the fibers 3 connect the abutting faces 10, 11, the fibers 3 guide light received at one of the abutting faces 10, 11 and emit the light at the respective opposed abutting face 11, 10. On the one hand, the diameter of the glass element 9 or multi-fiber light guide 1 may be larger than 5 mm, optionally larger than 15 mm, optionally larger than 25 mm and/or smaller than 50 mm, optionally smaller than 40 mm, optionally smaller than 30 mm. On the other hand, the thickness of the glass element 9 or multi-fiber light guide 1 may be larger than 0.3 mm, optionally larger than 0.6 mm, optionally larger than 1 mm and/or smaller than 2 mm, optionally smaller than 1.6 mm, optionally smaller than 1.3 mm. This way, the ratio of the diameter to thickness of the glass element 9 or multi-fiber light guide 1 may be between 2 and 170, optionally between 16 and 25. Such dimensions provide a broad field of applications of the multi-fiber light guide 1, such as cover glasses of electronic devices, and at the same time ensure a sufficient mechanical stability.

The interfaces between the cores 5 and the cladding 7 extend in transverse direction to the abutting faces 10, 11 and may constitute weakening zones. To improve the strength of the multi-fiber light guide 1, in particular the strength of the weakening zones, the abutting faces 10, 11 are subjected to an ion-exchange process so that ion-exchange layers 13 are formed at the surface of the abutting faces 10, 11.

To achieve a continuous ion-exchange layer, it is optional that the glasses of both the cores 5 and the cladding 7 have compositions with alkali oxides. Optionally, the total alkaline content of the glass of the cores 5 and/or the cladding 7, or optionally also the shell 17, in particular the combined alkaline content, is above 3 wt %, optionally above 5 wt %, especially in a case, when the amount of alkali ions with smaller ionic radius exceeds the amount of alkali ions with bigger ionic radius. Beneficially, the ratio of the amount of alkali ions with smaller ionic radius to the amount of alkali ions with bigger ionic radius in mol % is larger than 1.5, optionally larger than 2, optionally larger than 2.2. In some cases, alkali ions with big ionic radii are absent, or rather their amount is extremely low. Due to an alkali content of above 5 wt %, a sufficient and in particular improved chemical exchange can be achieved, so that a sufficient amount of compressive stress can be imparted into the glass of the cores 5, the cladding 7 and/or, the shell 17. Ideally, the glass of the cores 5 has a lower alkaline content to that of the cladding 7. This way, the compressive stress imparted into the cores 5 and/or the cladding 7 can be individually adjusted for specific applications and/or glass compositions.

In the ion-exchange process the alkali ions of the glasses are partly exchanged by heavier alkali ions having a larger ion radius. This way, the ions impart a compressive stress to the glass within the ion-exchange layer 13. According to the ion exchange process, Na-ions are leached from the glass of the cores 5 and/or the cladding 7 due to diffusion. Typically, and depending on the time the exchange process takes, alkaline ions with larger atomic radii, mostly K-ions, penetrate into the glass of the cores 5 and/or cladding 7 to form the ion-exchange layer 13. The penetration depth of alkaline ions with larger atomic radii in the glass of the cores 5 and/or cladding 7 is optionally larger than 2 μm after 10 hours of ion exchange, optionally larger than 2.5 μm. After 20 hours, the penetration depth may be between 3 μm and 35 μm or higher, in particular after more than 20 hours of ion exchange. In order to create a sufficient high compressive stress at the surface and optionally allow a subsequent polishing step, a penetration depth of above 1.5 μm is optional. It may be possible that the penetration depth of larger alkaline ions in the cores 5 and hence the DoL (depth of the ion exchange layer) is larger than that of the cladding 7. Beneficially, the penetration depth of alkaline ions with larger atomic radii in the cores 5 is less than the penetration depth of alkaline ions with larger atomic radii in the cladding 7. Optionally, the difference of the penetration depth of alkaline ions with larger atomic radii in the cores 5 and the cladding 7, or the differences of the DoL in the cores and cladding, respectively, is between a factor of 2 and a factor of 20, in particular it is at least a factor of 10 after 20 or 30 hours.

This way, effects due to the ion exchange on optical properties, such as stress birefringence of the glass of the cores 5, may be very low or even absent, so that the desired optical properties of the cores 5 can be kept during and after the ion exchange process. At the same time, compressive stress, at least an enhanced mechanical stability, can be imparted into the cladding. This way, cracks that may grow and/or propagate through the cladding 7 and in particular between the cores 5 or fibers or even propagate transversely through the entire glass element 9 or multi fiber light guide 1 can be prevented or at least reduced. Further, due to a different level of compressive stress and/or compositions of glass of the cores 5 and cladding 7, a propagation of cracks may be hindered at their interfaces. Generally, if the ion-exchange layer 13 is produced by fully immersing the glass element into a salt bath, the ion exchange occurs at the entire surface of the glass element 9. A continuous lateral compression of the glass element 9 can therefore be achieved. Further, a cross-diffusion between the core 5 and the cladding 7 at the surface or ion exchange layer 13 is possible. This may result in a gradient in depth compression, which may increases from deeper glass regions to the faces (10, 11). Therefore, optionally, the depth compression at the faces (10, 11) is stronger than in deeper glass regions. Typically, according to an optional embodiment, the ion-exchange layer 13 also extends along the outer circumferential surface or shell 17 which connects and extends between the two abutting faces 10, 11.

Figure 2:
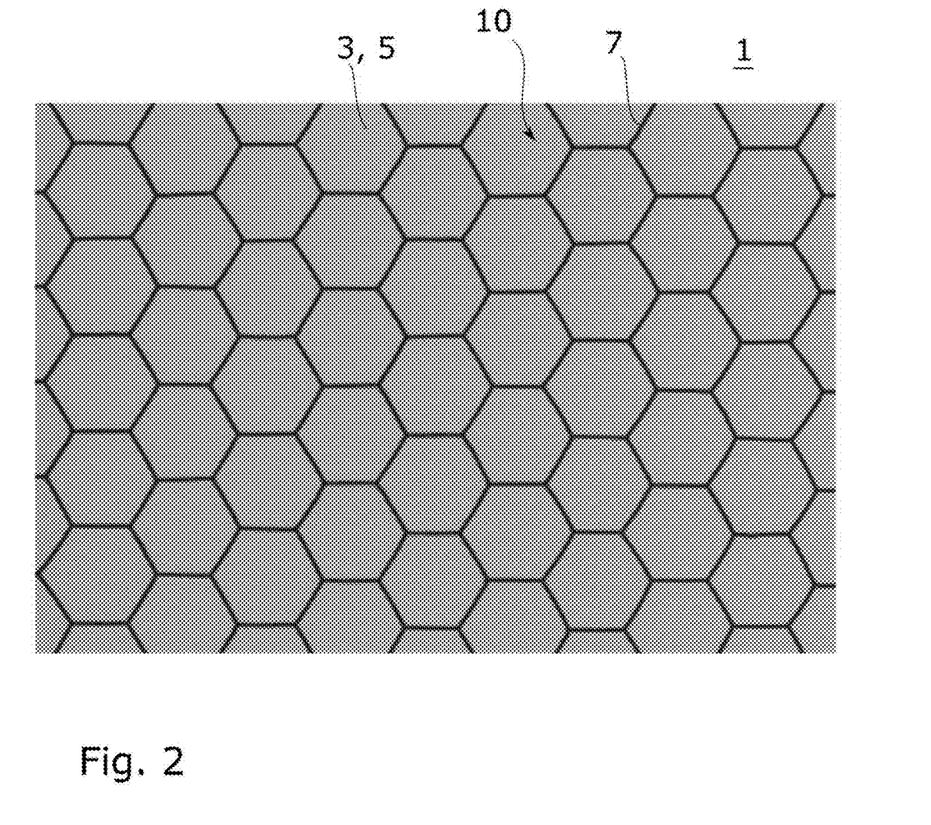
FIG. 2 shows a photographic image of an abutting face of a multi-fiber light guide.

FIG. 2 shows a photographic image of an abutting face 10, 11 of a multi-fiber light guide 1. Generally, as in the example of FIG. 2, the cores 5 may have a hexagonal cross-section. Further, generally and without restriction to the shape of the cross-section of the cores 5, the cores 5 may be arranged in a hexagonal pattern. These features can be advantageous in several respects. If an image of a pixel display is transferred from one abutting face to the opposed face, the hexagonal pattern may help to avoid moiré patterns at the abutting face where the light exits. Further, the honeycomb-like structure of the interfaces between cores 5 and cladding may increase mechanical stability.

According to a further embodiment which is also realized in the example of FIG. 2, the glass of the cladding 7 may be at least partially light absorbing. This is generally advantageous to reduce cross-talk or light leaching between the fibers 3. According to one embodiment, which is also realized in the embodiment of FIG. 2, the glass of the cladding 7 is a black glass. However, the glass may also be partially absorbing as it is the case for colored glasses. In this case, the glass has a spectrally dependent and spectrally varying absorption. For example, the glass may be brown, red or purple colored.

Figure 3:
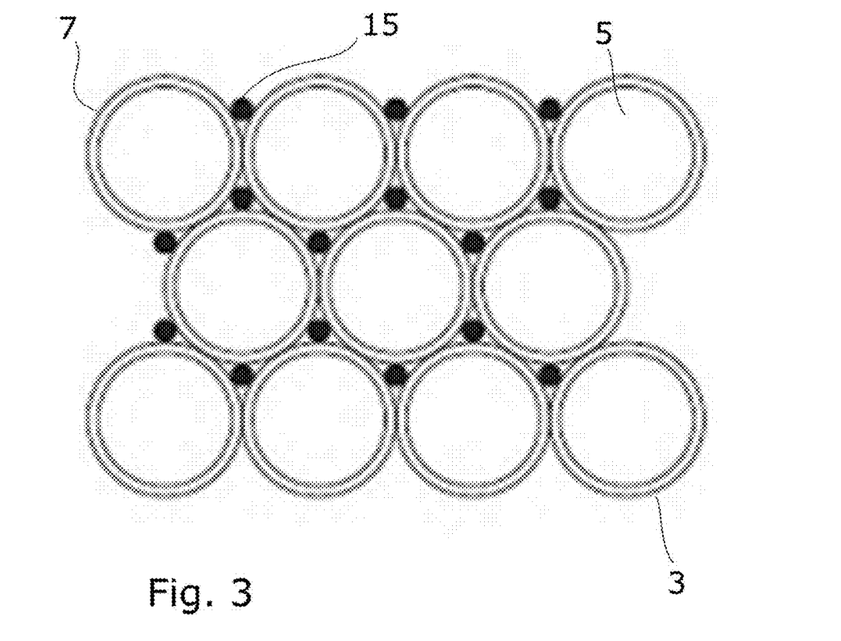
FIGS. 3 and 4 show two examples of light guides with light absorbing elements.
Figure 4:
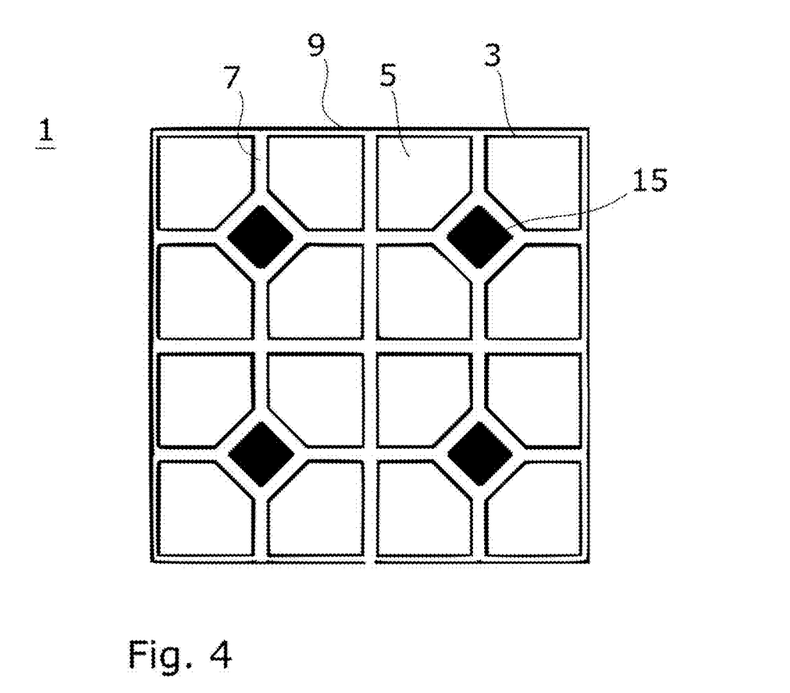

Another possibility to reduce cross-talk between the fibers 3 is to provide additional absorbing fibers within the glass element 9 which are located between the cores 5 of the light guiding fibers. Two examples of these embodiments are shown in FIG. 3 and FIG. 4. FIG. 3 shows a stack of individual light guiding fibers 3 with light absorbing fibers 15 being located in interstices between the light guiding fibers 3. The fibers 3, 15 of the stack can be fused together to form a rigid rod. Multi-fiber light guides 1 can then be produced by cutting sections of desired dimensions from the rod.

FIG. 4 shows an example of a multi-fiber light guide 1 with the fibers fused together to form a rigid continuous glass element 9. In this example the cores 5 are arranged in a square pattern. At every second intersection of four cores 5 a light absorbing fiber 15 is arranged. Both the cores 5 and the light absorbing fibers 5 are surrounded by the cladding 7. The additional light absorbing fibers 15 within the rigid glass element 9 provide an extra-mural absorption to reduce cross-talk or to block light which obliquely transits the multi-fiber light guide 1.

In this example, the multi-fiber light guide 1 includes three different glasses, i.e., the glass of the cores 5, the glass of the cladding 7 and the glass of the light absorbing fibers 15. The glass of the light absorbing fibers 15 may be similar to one of the other glasses but includes light absorbing pigments or dyes such as coloring ions.

Figure 5:
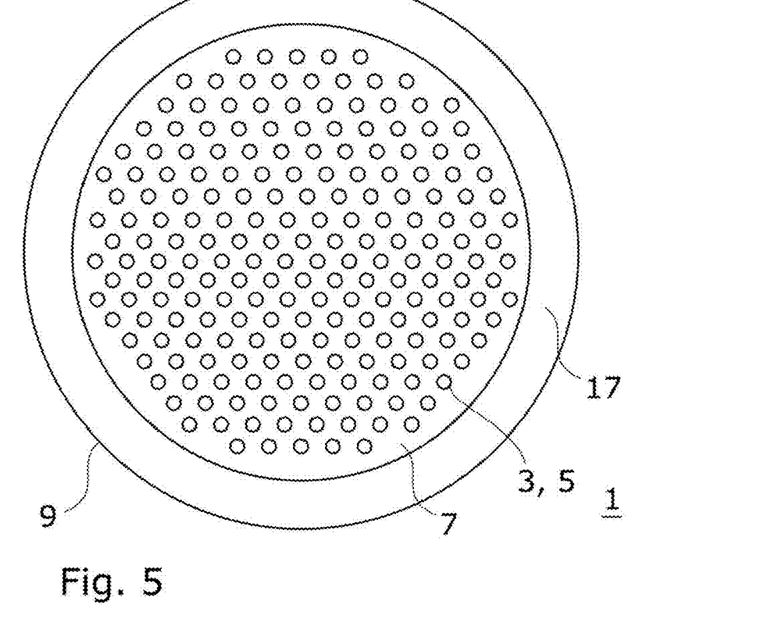
FIG. 5 shows a multi-fiber light guide with a circumferential shell.

FIG. 5 shows a further embodiment of a multi-fiber light guide 1. This light guide includes a circumferential shell 17, which extends about the central arrangement of fibers 3. Specifically, it is advantageous if this shell 17 is made of glass as well so that the shell 17 forms an integral part of the glass element 9 of the light guide 1. Accordingly, the glass element 9 includes a glass shell 17, which encompasses the bundled fibers 3 or the cladding 7 in which the cores 5 are embedded, respectively. This way, the shell also forms an outer circumferential section of the abutting faces 10, 11.

According to a refinement, the glass of this shell 17, in particular the composition of the glass of the shell 17 and optionally the alkaline content of the shell 17, may differ from the glasses, the composition of the glasses, and/or the alkaline content of the cores 5 and the cladding 3. Thus, in this embodiment the glass element 9 includes three different glasses, i.e. the glasses of the cores 5, the cladding 7, and the shell 17. Further, it is advantageous if the glass shell 17 is chemically strengthened like the cores 5 and the cladding 7 so that an ion exchange layer 13 can be formed at the abutting faces 10, 11 by ion exchange, which optionally continuously extends over the entire surface, in particular over the entire abutting faces 10, 11 of the glass element 9 or the multi-fiber light guide 1.

To improve at least the lateral mechanical strength of the glass element 9 or the multi-fiber light guide 1, advantageously, the width of the shell 17 is larger than the width of the cladding 7, in particular the width of the cladding 7 between the cores 5. An optional width of the shell is larger than 1% of the total outer diameter of the of the glass element 9 or the multi-fiber light guide 1, optionally, larger than 2%, optionally larger than 4% and/or smaller than 10%, optionally smaller than 8%, optionally smaller than 6% of the total outer diameter of the of the glass element 9 or the multi-fiber light guide 1. In some special cases, such as in case of a grinded glass element 9, the width of the shell 17 may be smaller than 1% outer diameter of the of the glass element 9.

The improved mechanical strength of multi-fiber light guides in the form of faceplates was investigated with a ball drop test. Faceplate samples of chemically toughened faceplates were compared to faceplates that have not been chemically toughened. All samples had a diameter of about 13 mm. The samples were positioned on a steel plate without damping material. A steel ball was dropped vertically onto the sample. The test was repeated with increased weight of the steel ball until the sample broke. The results are listed in the following table:

|  | Not toughened samples | Toughened samples |
| --- | --- | --- |
| Average weight of ball [g] | 3.6 | 6.2 |
| Standard deviation of the ball weight [g] | 3.0 | 3.3 |
| Minimum weight of steel ball [g] | 1 | 1 |
| Maximum weight of steel ball [g] | 7 | 14 |
| Tested samples | 47 | 29 |
| Number of samples broken with steel ball of 1 g weight | 27 | 6 |
| Number of samples broken with steel ball of 7 g weight | 20 | 21 |
| Number of samples broken with steel ball of 14 g weight | 0 | 2 |
| Percentage of samples broken with steel ball of 1 g weight | 57.4% | 20.7% |
| Percentage of samples broken with steel ball of 7 g weight | 42.6% | 72.4% |
| Percentage of samples broken with steel ball of 14 g weight | 0.0% | 6.9%. |

As it is evident from the above table, the mechanical strength against impact or shock is significantly increased by the chemical toughening. Nearly 80% of the chemically toughened samples withstand the 1 g ball drop test, whereas more than half of the not toughened samples already break with the 1 g weight.

Further, the ion exchange for the chemical toughening also does not adversely affect the optical properties of the multi-fiber light guide.

Figure 6:
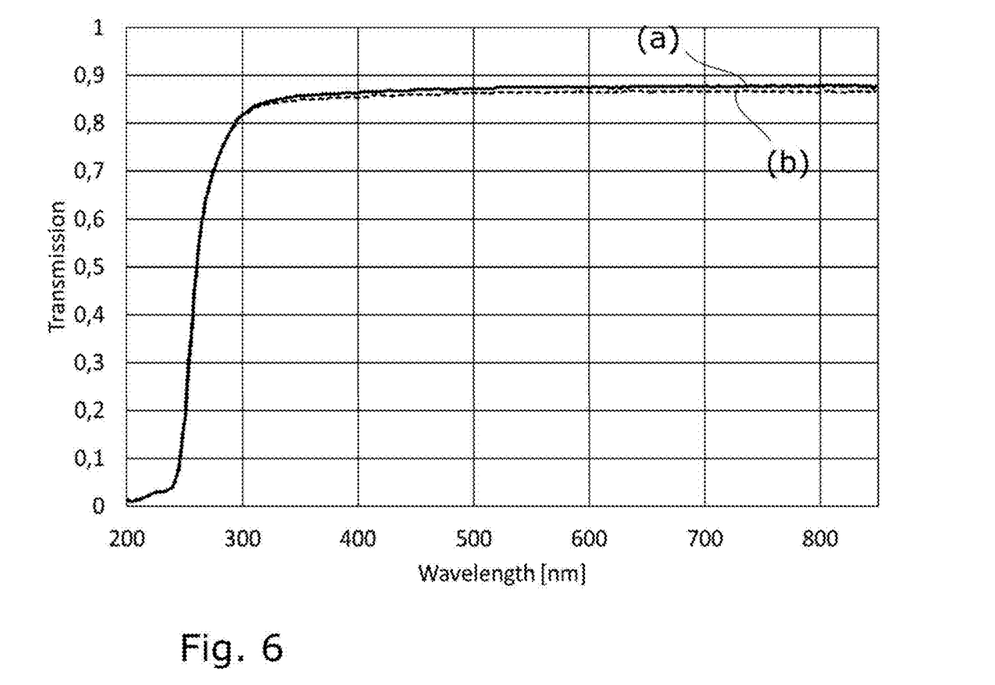
FIG. 6 shows diagrams of the transmission of a chemically toughened light guide in comparison to a not toughened light guide.

FIG. 6 shows diagrams of the transmission of a chemically toughened light guide in comparison to a not toughened light guide. For comparison, the transmission of a multi-fiber light guide was measured before toughening. Then the light guide was subjected to an ion-exchange for 20 hours. After this ion exchange procedure and chemical toughening, the transmission measurement was repeated. Curve (b) is the transmission before the ion exchange, and curve (a) represents the transmission after the ion-exchange process or chemical toughening, respectively. As can be seen from the curves, the transmission remains nearly unaffected. Surprisingly, the transmission is even slightly higher after the ion exchange which may be attributed to refractive index changes in the ion exchange layer 13.

The multi-fiber light guide 1 according to this disclosure is particularly suited as a window for optical sensors. Therefore, according to one embodiment, an optical sensor arrangement is provided including a sensor element such as, e.g. a photodiode, whereby the sensor element is encased in a housing which includes a multi-fiber light guide according to this disclosure. The multi fiber light guide is arranged so as to guide light from outside of the housing to the sensor element. To use a multi-fiber light guide as a window is further particularly advantageous if the sensor arrangement also includes a light source to probe and illuminate the object to be sensed by the sensor. In this case, the light guide can effectively suppress a direct signal path from the light source to the sensor, which results from an internal reflection at the outer abutting face of the window. This suppression allows to use a single common window for both the light source and the sensor. Accordingly, in a refinement of this embodiment the sensor arrangement includes a light source, optionally a semiconductor light source such as a light emitting diode (LED) or laser diode (LD) within the housing, whereby the light source and the sensor element are so positioned with respect to the multi-fiber light guide that the light source emits light through the multi-fiber light guide, and the sensor element receives light through the same multi-fiber light guide.

Figure 7:
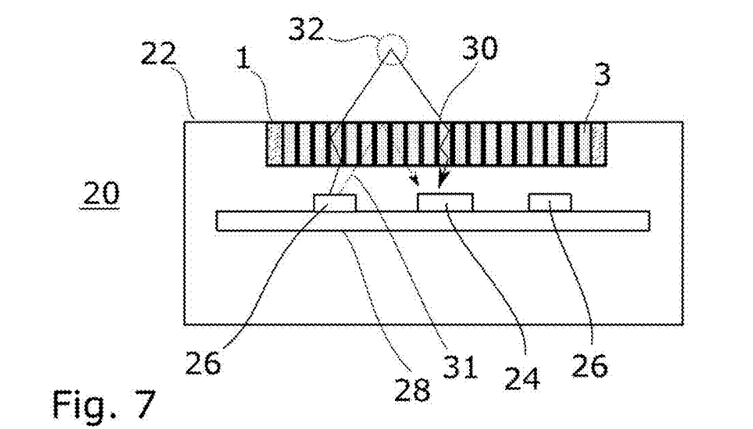
FIG. 7 shows a sensor arrangement with a multi-fiber light guide.

In FIG. 7 such a sensor arrangement with a multi-fiber light guide 1 is shown. The sensor arrangement includes a housing 22. The multi-fiber light guide 1, optionally in the form of a faceplate forms a part of the housing 22 so that light can be transmitted inside the housing and vice versa. The sensor arrangement 20 includes a sensor element 24. In an optional embodiment, a light source 26 is included as well. The sensor element 24 and the light source 26 are mounted on a common printed circuit board 28 facing the multi-fiber light guide 1. As shown, the optical sensor arrangement 20 may also include more than one light source 26. In the example shown, the sensor element 22 is arranged between two light sources 26.

To illustrate the effect of the faceplate as a window for the sensor element 24 and the light source 26, two light rays 30, 31 are sketched. Light ray 31 would be a possible path if the window in the housing 22 would be a simple transparent plate. This way, the light ray 31 may be reflected at the outer face of the window and could then directly impinge onto the sensor element 24 without interaction within an external interaction zone 32. If instead a multi-fiber light guide 1 is used as a window, the light ray 31 is guided to the outer abutting face within a light guiding fiber 3. Even if the light ray would be reflected at the outer face, it would be guided back within the fiber 3 and therefore cannot reach the sensor element. This way, unwanted background signals are minimized. After being emitted from the sensor arrangement 22, the light ray can interact with an external interaction zone 32, re-enter the housing 22 through the light guide 1 and finally reach the sensor element 24.

To avoid background noise caused by a light ray 30, one would need to use separate windows for the light source 26 and the sensor element 24. In contrast, with the multi-fiber light guide, a single window with large enough diameter is sufficient and allows for a higher sensor and/or light source density within the same region. This brings higher integration in terms of optical sensing.

Generally, one optional embodiment of a sensor arrangement 20 is an optical heart rate monitor. Further, the sensor arrangement 20 may be a wearable device such as a smart watch. In case of a wearable device, e.g. in form of a wrist watch with an optical heart rate monitor, the housing is typically fastened to the body with the window or faceplate, respectively, contacting the skin. A wearable device is particularly prone to impacts, e.g., if the device is taken off and placed onto a hard surface. Due to the chemically toughened abutting faces, however, the probability for breakage or at least chipping of the outer surface due to impact stress is lowered. The multi-fiber light guide with the glass element 9 according to this disclosure is also considerably more durable compared to plastic windows which are frequently used for wearable devices. These plastic windows degrade over time and have performance issues with regards to waterproofing, durability and aesthetics.

In the above described examples, the multi-fiber light guide 1 is plate shaped. However, it is also contemplated to use elongated light guides with the length of the light guiding fibers 3 being greater than the largest lateral dimension of the glass element 9. One example is a dental rod. These rods are used to guide light to a treatment zone, e.g. to cure photo-polymerizable fillers for dental treatments.

Figure 8:
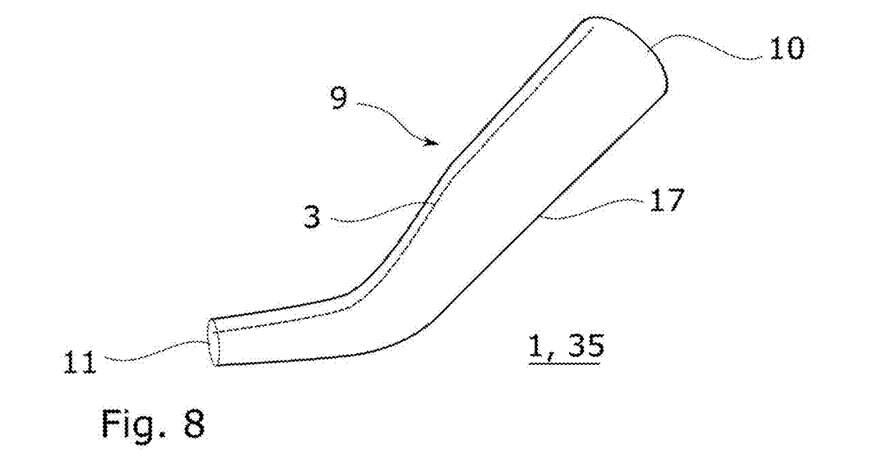
FIG. 8 shows a multi-fiber light guide shaped as a dental rod.

A dental rod 35 as a further embodiment of a multi-fiber light guide 1 is shown in FIG. 8. The dental rod 35 is shaped as an elongated light guide so that the length of the light guiding fibers 3 is greater than the largest lateral dimension of the glass element 9. In the figure, a single light guiding fiber 3 is drawn as a hatched line to illustrate the orientation and arrangement of the light guiding fibers. As not only the abutting faces 10, 11 of the multi-fiber light guide 1, but also the shell 17 are chemically toughened, the glass element 9 is stabilized to withstand impact shocks. For example, the toughening may help to avoid breakage, if the tool with the dental rod is accidentally dropped.

In addition, the embodiment of FIG. 8 is an example of further refinements of the multi-fiber light guide 1. According to a first refinement, the two abutting faces 10, 11 may differ in their cross section. This difference may include at least one of the surface area and the shape or outline of the abutting faces 10, 11. In the example, the surface areas of the cross-sections are different, with the surface area of abutting face 11 being smaller than the surface area of opposite abutting face 10. Accordingly, the multi-fiber light guide 1 may be tapered, as it is also realized in the depicted example.

Further, generally, the multi-fiber light guide 1 may include at least one bend. The aforementioned features may also be realized with a plate shaped multi-fiber light guide but are generally more effective for an elongated light guide 1. Both a bend and a taper of the glass element 9 may be produced by hot forming. A taper is generated by heating and axially drawing the glass element. This way, the number of fibers 3 remains constant. However, the diameter of the fibers reduces along the taper.

Independent from the various shapes of a light guide 1 as discussed herein, the multi-fiber light guide may be produced using a drawing process starting with an appropriate preform. By repeated drawing, the fiber diameters are sequentially reduced until fibers with small, in particular microscopic lateral dimensions are obtained.

Figure 9:
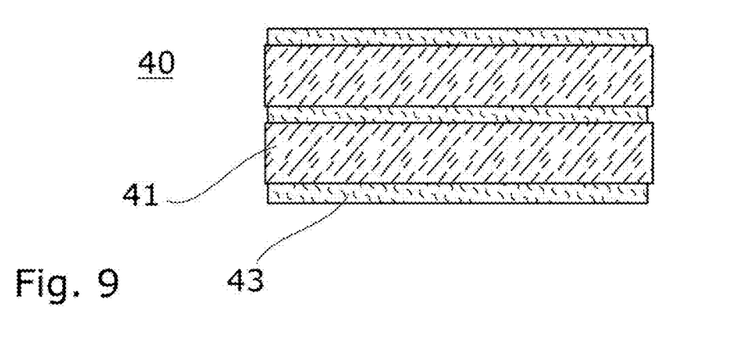
FIGS. 9, 10, 11, and 12 illustrate method steps to produce a multi-fiber light guide.
Figure 10:
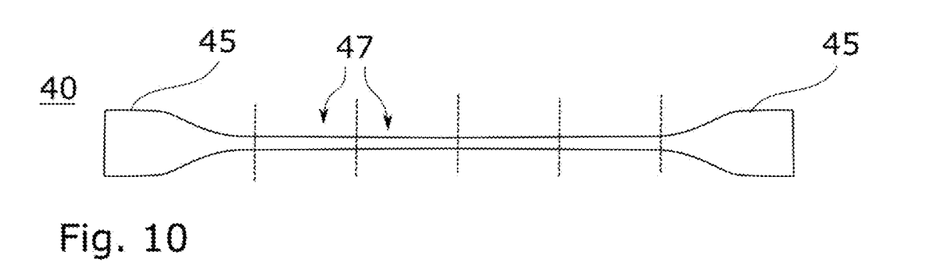
Figure 11:
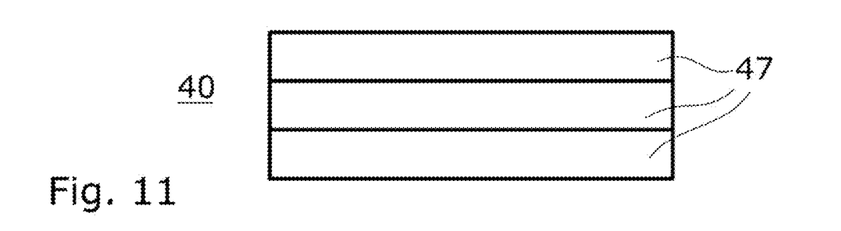
Figure 12:
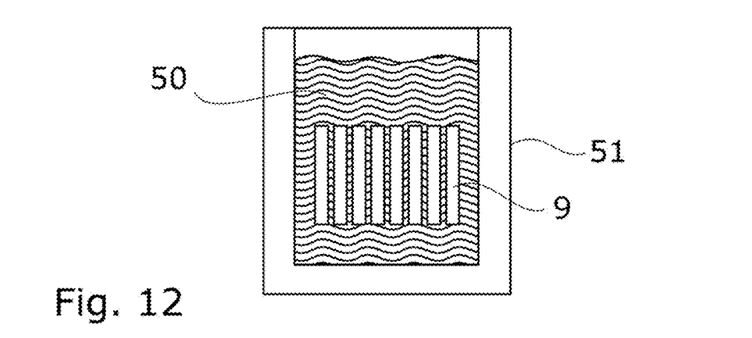

Specifically, the multi-fiber light guide 1 may be produced with a method including the following steps, which are also illustrated with respect to FIG. 9 to FIG. 12:

providing a preform 40 with at least one rod 41 of a first glass and at least one glass element 43 of a second glass having a lower refractive index than the first glass, the preform 40 being assembled, so that the rod 41 is surrounded by the second glass;

heating the preform and fusing the rods 41 to the at least one glass element 43; and drawing the preform 40 to increase its length and reduce the lateral dimensions of the rods 41;

cutting the drawn preform 40 into sections 47; and assembling the sections to form a further preform 40, wherein the steps of assembling the sections 47 to a new preform, drawing the new preform, and cutting the drawn preform 40 into sections 47 is optionally repeated at least once;

cutting sections 47 from the preform 40 to obtain glass elements 9 as described herein, including a multitude of light guiding fibers 3 with a core of the first glass surrounded by a cladding of the second glass;

immersing the glass elements into a salt bath 50 containing alkali ions to effect an ion exchange with the alkali ions in the glasses of the glass element 9 and to form an ion exchange layer 13 at the surface of the glass element which exerts a compressive stress to the glass.

Optionally, the coefficient of thermal expansion (CTE) of the first glass, in particular the glass of the desired cores 5, is different to the CTE of the second glass, in particular the desired glass of the cladding 7. To prevent a mismatch, especially a tensile stress during further steps, it is optional that the CTE of the first glass, in particular the glass of the desired cores 5 is smaller than the CTE of the second glass, in particular the desired glass of the cladding 7. Advantageously, in particular to generate at least a slight compression, the CTE of the first glass, in particular the glass of the desired cores 5, is larger than the CTE of the second glass, in particular the desired glass of the cladding 7. The difference of the CTE of the first glass and the CTE of the second glass is being specified as difference of CTE (cladding/core)= CTE second glass−CTE first glass. According to this specification, a difference of CTE (cladding/core) between +3.5 ppm/K and −1 ppm/K is optional. While a positive value causes a compression of the glass of the cladding 7, a negative value causes an increased tensibility of the glass of the cladding 7.

In order to achieve a sufficient compression, a difference of CTE (cladding/core) below 3 ppm/K is optional. In case the glass element 9 includes a shell 17, to prevent a mismatch, especially a tensile stress, it is optional that the CTE of the glass of the cladding 7 is smaller than the CTE of the glass of the shell 17. Advantageously, in particular to generate at least a slight compression, the CTE of the glass of the shell 17 is larger than the CTE of the glass of the cladding 7. Accordingly, the CTE of the glass of the shell 17 is different to the CTE of the glass of the cladding 7. The difference of the CTE of the glass of the shell and the CTE of the glass of the cladding is being specified as difference of CTE (shell/cladding)=CTE glass of the shell 17−CTE glass of the cladding 7. According to this specification, a difference of CTE (shell/cladding) between +5 ppm/K and −1 ppm/K is optional. While a positive value causes a compression of the shell 17 on the cladding 7, a negative value causes an increased tensibility of the shell 17.

FIG. 9 shows the preform 40 in a cross-sectional view. The glass element 43 may be a single element with through holes therein, into which the rods 41 are inserted. Alternatively, a multitude of glass elements 43 may be used which are arranged between the rods 41 and cover the outward facing sides of the rods 41.

The rods 41 are fused to the one or more glass element 43, and the preform 40 is drawn to increase its length and reduce the lateral dimensions of the rods 41. Fusing may in particular be effected by the drawing step which also requires heating to soften the glass. FIG. 10 shows the drawn preform. The ends 45 of the preform 40 still have the original lateral dimensions, as the preform is clamped at its ends to apply a drawing force. The drawn part is then cut into sections 47. These sections are put together to form a further preform 40 as shown in FIG. 11. The steps of assembling and drawing the preform 40 and cutting the drawn preform 40 into sections 47 may be repeated until the desired fiber dimensions are reached. Then, sections 47 are cut from the drawn preform which are glass elements 9 as described above. The sections 47 may be thin slices, which form faceplates as exemplarily shown in FIG. 1 or FIG. 7 or may be elongated as in the example of FIG. 8. Finally, as shown in FIG. 12, the glass elements 9 are immersed into a salt bath 50 within a container 51. Suitable for toughening glass elements with sodium containing glasses is a molten salt bath including molten potassium nitrate.

Figure 13:
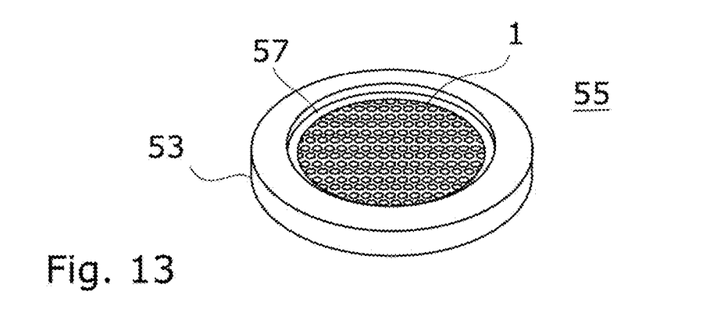
FIG. 13 shows an assembly with a glass element.

According to a variant of the method, the multi-fiber light guide 1 may be further processed before chemical strengthening. Specifically, the multi-fiber light guide 1 may be sealed into a socket or mount so that an assembly with the multi-fiber light guide 1 fixed in the socket is obtained. After sealing, the assembly with the multi-fiber light guide 1 and the socket is subjected to an alkali ion-exchange and chemically toughened. A composite 55 with a socket 53 and the multi-fiber light guide 1 sealed therein is shown in FIG. 13. Of course, according to an alternative embodiment, the chemical toughening of the multi-fiber light guide 1 may also be performed before producing the assembly. If the multi-fiber light guide 1 is chemically toughened while sealed in the socket 53, the ion exchange may be suppressed in sections of the multi-fiber light guide that are sealed to the socket 53 and are therefore covered. Vice versa, if a glass solder with alkali oxide content is used, the glass solder may undergo an ion-exchange process as well so that the glass solder exhibits an ion-exchange layer. Thus, it can be verified from the assembly 55, whether the multi-fiber light guide 1 was sealed to the socket 53 before or after the chemical toughening.

The socket 53 may be a metal, optionally a stainless steel, a ceramic or another glass. In one embodiment, the socket 53 is a metal ring. However, the socket 53 may also be a housing part, e.g. of a housing for a wearable electronic device. According to a further embodiment which is also realized in the depicted example, the multi-fiber light guide 1 is soldered to the socket 53. The solder 57 between the multi-fiber light guide 1 and the socket 53 may be a glass solder.

| List of reference signs | |
| --- | --- |
| 1 | Multi-fiber light guide |
| 3 | Fiber |

-continued

| List of reference signs | |
|---|---|
| 5 | Core of fiber 3 |
| 7 | Cladding |
| 9 | Glass element |
| 10, 11 | Abutting face of light guide 1 |
| 12 | Side of light guide 1 |
| 13 | Ion exchange layer |
| 15 | Absorbing fiber |
| 17 | Shell |
| 20 | Optical sensor arrangement |
| 22 | Housing of optical sensor arrangement 20 |
| 24 | Sensor element |
| 26 | Light source |
| 28 | Printed circuit board |
| 30, 31 | Light ray |
| 32 | Interaction zone |
| 35 | Dental rod |
| 40 | Preform |
| 41 | Rod |
| 43 | Glass element |
| 45 | End of 40 |
| 47 | Section cut from drawn preform 40 |
| 50 | Salt bath |
| 51 | Container |
| 53 | Socket |
| 55 | Assembly |
| 57 | Solder. |

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A multi-fiber light guide, comprising:
a plurality of light guiding fibers, each of the plurality of light guiding fibers including a glass core which is elongated, the plurality of light guiding fibers thereby including a plurality of the glass core which includes a glass;
a glass cladding which includes a glass, the plurality of the glass core being surrounded by the glass cladding such that the glass cladding with the plurality of the glass core form a glass element which is rigid and continuous, the plurality of the glass core having a higher refractive index than the glass cladding and thereby being configured such that a light can be guided by a total reflection along the plurality of the glass core, the glass element of the multi-fiber light guide including two abutting faces, with the plurality of the glass core ending in respective ones of the two abutting faces and thereby being configured such that the light can be guided along the plurality of the glass core from a respective one of the two abutting faces to another respective one of the two abutting faces, the glass element further including a glass shell which encompasses the glass cladding with the plurality of the glass core which are embedded, the glass shell extending between the two abutting faces; and
an ion exchange layer at each of the two abutting faces, the glass of the plurality of the glass core and the glass of the glass cladding including a plurality of alkali ions, which are at least partly exchanged by a plurality of alkali ions of a higher atomic number within the ion exchange layer at each of the two abutting faces, exchanged ones of the plurality of alkali ions within the ion exchange layer imparting a compressive stress at the two abutting faces, the ion-exchange layer also extending along the glass shell of the glass element.

2. The multi-fiber light guide according to claim 1, wherein the multi-fiber light guide includes at least one of the following:
(a) a penetration depth of the ion-exchange layer in the plurality of the glass core is different from a penetration depth of the ion-exchange layer in the glass cladding;
(b) a coefficient of thermal expansion of the plurality of the glass core is different from the coefficient of thermal expansion of the glass cladding; and
(c) the glass shell includes a glass, the coefficient of thermal expansion of the glass of the glass shell being different from the coefficient of thermal expansion of the glass of the glass cladding.

3. The multi-fiber light guide according to claim 1, wherein the glass element is a disc, a thickness of the disc being smaller than a shortest lateral dimension of the disc.

4. The multi-fiber light guide according to claim 1, wherein the multi-fiber light guide has an elongated shape, and the length of the plurality of light guiding fibers is greater than a largest lateral dimension of the glass element.

5. The multi-fiber light guide according to claim 1, wherein the multi-fiber light guide includes at least one of the following:
the two abutting faces differ in a surface area of respective ones of the two abutting surfaces;
the two abutting faces differ in a shape of respective ones of the two abutting surfaces; and
the glass element includes at least one bend.

6. The multi-fiber light guide according to claim 1, wherein the multi-fiber light guide includes at least one of the following:
the plurality of the glass core are arranged in a plurality of hexagonal pattern;
the glass of the glass cladding is light absorbing;
the glass element of the multi-fiber light guide comprises a plurality of light absorbing fibers;
a center-to-center distance of adjacent ones of the plurality of light guiding fibers is from 2 µm to 500 µm.

7. The multi-fiber light guide according to claim 1, wherein the multi-fiber light guide is configured for being a part of an assembly which includes a socket and the multi-fiber light guide sealed into the socket.

8. The multi-fiber light guide according to claim 7, wherein the multi-fiber light guide is configured for being chemically toughened while sealed in the socket.

9. An optical sensor arrangement, comprising:
a housing including a multi-fiber light guide, the multi-fiber light guide including:
a plurality of light guiding fibers, each of the plurality of light guiding fibers including a glass core which is elongated, the plurality of light guiding fibers thereby including a plurality of the glass core which includes a glass;
a glass cladding which includes a glass, the plurality of the glass core being surrounded by the glass cladding such that the glass cladding with the plurality of the glass core form a glass element which is rigid and continuous, the plurality of the glass core having a higher refractive index than the glass cladding and thereby being configured such that a light can be guided by a total reflection along the plurality of the glass core, the glass element of the multi-fiber light guide including two abutting faces, with the plurality of the glass core ending in respective ones of the two abutting faces and thereby being configured such that the light can be guided along the plurality of the glass core from a respective one of the two abutting faces to another respective one of the two abutting faces, the glass element further including a glass shell which encompasses the glass cladding with the plurality of the glass core which are embedded, the glass shell extending between the two abutting faces; and an ion exchange layer at each of the two abutting faces, the glass of the plurality of the glass core and the glass of the glass cladding including a plurality of alkali ions, which are at least partly exchanged by a plurality of alkali ions of a higher atomic number within the ion exchange layer at each of the two abutting faces, exchanged ones of the plurality of alkali ions within the ion exchange layer imparting a compressive stress at the two abutting faces, the ion-exchange layer also extending along the glass shell of the glass element;

a sensor element encased in the housing, the multi-fiber light guide configured for guiding a light from outside of the housing to the sensor element.

10. The optical sensor arrangement according to claim 9, further comprising a light source within the housing, wherein the light source and the sensor element are positioned with respect to the multi-fiber light guide such that the light source is configured for emitting the light through the multi-fiber light guide and the sensor element is configured for receiving the light through the multi-fiber light guide.

11. The optical sensor arrangement according to claim 9, wherein the optical sensor arrangement is an optical heart rate monitor.

12. The optical sensor arrangement according to claim 9, wherein the optical sensor arrangement is a wearable device.

13. A method for producing a multi-fiber light guide, the method comprising the steps of:

providing a first preform with at least one rod of a first glass and at least one first glass element of a second glass having a lower refractive index than the first glass, the first preform being assembled such that the at least one rod is surrounded by the second glass;

heating the first preform and fusing the at least one rod to the at least one first glass element;

drawing the first preform to increase a length of the first preform and to reduce a lateral dimension of the at least one rod;

cutting the first preform, which has been drawn, into a first plurality of sections;

assembling the first plurality of sections to form a second preform;

cutting a second plurality of sections from the second preform to obtain a plurality of second glass elements comprising a plurality of light guiding fibers including a core of the first glass surrounded by a cladding of the second glass, the core being a glass core, the cladding being a glass cladding; and immersing the plurality of second glass elements into a salt bath including a plurality of alkali ions to effect an ion exchange with a plurality of alkali ions in a plurality of glasses of respective ones of the plurality of second glass elements and to form an ion exchange layer at a surface of the respective ones of the plurality of second glass elements which exerts a compressive stress to the plurality of glasses, wherein the respective ones of the plurality of second glass elements each including two abutting faces and a glass shell, a plurality of the glass core ending in respective ones of the two abutting faces and thereby being configured such that a light can be guided along the plurality of the glass core from a respective one of the two abutting faces to another respective one of the two abutting faces, the glass shell encompassing the glass cladding with the plurality of the glass core which are embedded, the glass shell extending between the two abutting faces, the ion-exchange layer also extending along the glass shell.

14. The method according claim 13, wherein the multi-fiber light guide is sealed into a socket, and wherein an assembly with the multi-fiber light guide and the socket is chemically toughened after sealing.

\* \* \* \* \*